United States Patent [19]

Blurton et al.

[11] 4,127,462

[45] Nov. 28, 1978

[54] DEVICE FOR THE DETECTION AND MEASUREMENT OF NOXIOUS GASES

[75] Inventors: Keith F. Blurton, Yorktown, N.Y.; John M. Sedlak, Norwalk, Conn.

[73] Assignee: Energetics Science, Inc., Elmsford, N.Y.

[21] Appl. No.: 776,419

[22] Filed: Mar. 10, 1977

Related U.S. Application Data

[62] Division of Ser. No. 621,554, Oct. 10, 1975, Pat. No. 4,042,464.

[51] Int. Cl.$^2$ ............................................. G01N 27/46
[52] U.S. Cl. ................................................. 204/195 R
[58] Field of Search .................... 204/1 T, 1 Y, 195 R

[56] References Cited

U.S. PATENT DOCUMENTS

| | | | |
|---|---|---|---|
| 3,291,753 | 12/1966 | Thompson | 429/40 |
| 3,382,103 | 5/1968 | Smith | 429/13 |
| 3,776,832 | 12/1973 | Oswin et al. | 204/195 R |
| 3,824,167 | 7/1974 | Oswin et al. | 204/195 R |
| 4,001,103 | 1/1977 | Blurton et al. | 204/195 R |

*Primary Examiner*—T. Tung
*Attorney, Agent, or Firm*—Larson, Taylor and Hinds

[57] ABSTRACT

Noxious gases are electrochemically detected and measured in the presence of carbon monoxide using a device employing an electrochemical cell whose sensing electrode comprises a carbon supported gold catalyst and is maintained at a fixed potential of about 0.4 volt to about 1.5 volt with respect to a reversible hydrogen electrode in said electrolyte of the electrochemical cell. In its preferred form the sensing electrode comprises carbon particles containing catalytic amounts of gold bonded to a hydrophobic material to provide a diffusion electrode.

13 Claims, 4 Drawing Figures

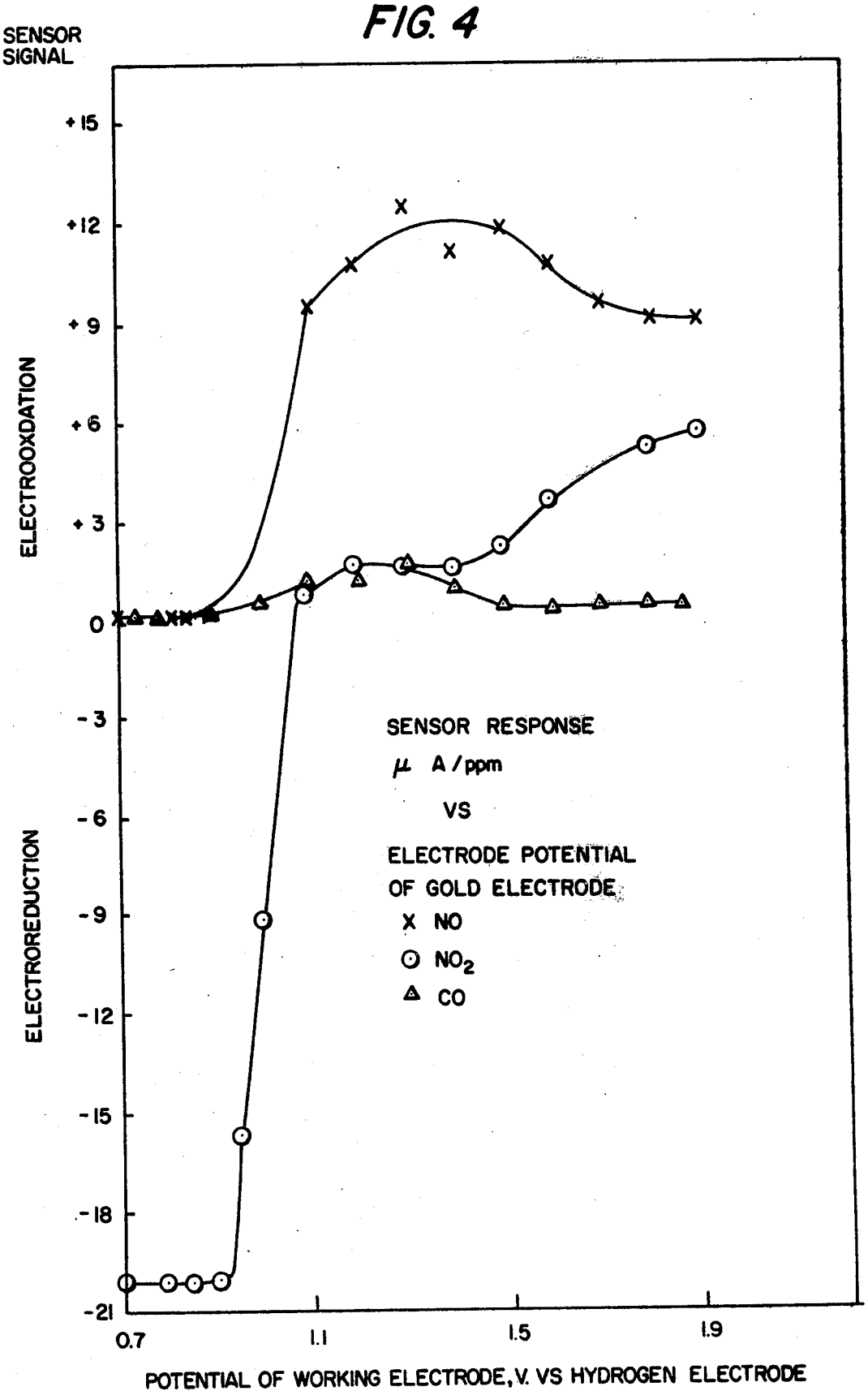

DEVICE FOR THE DETECTION AND MEASUREMENT OF NOXIOUS GASES

This is a division, of application Ser. No. 621,554 filed Oct. 10, 1975, now U.S. Pat. No. 4,042,464.

BACKGROUND OF THE INVENTION

1. Field of the Invention

The present invention relates to a device and method for the detection and measurement of gaseous pollutants such as nitric oxide, nitrogen dioxide, sulfur dioxide, mercaptans, hydrogen sulfide and the like in a variety of gas mixtures. More particularly, the invention is directed to the detection of these pollutants in the presence of high concentrations of carbon monoxide.

2. Discussion of the Prior Art

In recent times, a greater awareness has developed regarding the dangers of air pollution, particularly in urban or industrialized areas. Amongst the principle combustion contributions to air pollution are the products of the combustion process such as carbon monoxide and sulfur dioxide, the products of reactions between nitrogen and oxygen such as nitric oxide and nitrogen dioxide, and the by-products of industrial processes such as hydrogen sulfide and methyl mercaptan. It is not surprising, therefore, that pollutant concentrations in many areas is approaching levels known to be harmful to health.

In order to meet the needs arising in connection with pollution control of NO and $NO_2$, and other noxious gases such as $H_2S$, $SO_2$, methyl mercaptan, ethyl mercaptan and the like, extensive activity has been directed to the development and production of equipment useful in solving this problem. A problem encountered in the development of such equipment is the difficulties experienced in the detection of low concentrations of these gases in the presence of high concentrations of CO, a frequently encountered situation. Consequently, although many of these gases are known to be electrochemically active, the development of electrochemical instrumentation for these gases has been hindered by their lack of selectivity when detecting in the presence of CO.

One approach taken to improve the selectivity of the electrochemical sensors for these gases in the presence of CO has been to use a gold catalyst for the sensing electrode as described, for instance, in U.S. Pat. No. 3,776,832 to Oswin et al. This approach, however, has only been partially successful. For example, typical discrimination ratios for $NO_2$ and $H_2S$ in the presence of CO are $-1000/1$ and $2000/1$, respectively. (The negative signal for the $NO_2$/CO ratio indicates that $NO_2$ is electro-reduced whereas CO is electro-oxidized.) Therefore, 1000 ppm CO will give a signal equivalent to $-1$ ppm $NO_2$ (negative deflection on instrument meter), and 2000 ppm CO will give a signal equivalent to 1 ppm $H_2S$. In order to consider the practical influence of these ratios it is necessary to consider the typical ambient concentrations of 10 ppm CO, 20 ppb $NO_2$ and 5 ppb $H_2S$. Ten ppm CO will give a reading equivalent to $-10$ ppb $NO_2$ (a 50% error in $NO_2$ signal) and a reading equivalent to 5 ppb $H_2S$ (a 100% error in $H_2S$ signal). The magnitude of these percentage errors clearly points out the shortcomings of electrochemical instrumentation employing gold working electrodes in the detection of these pollutant gases in the presence of CO.

OBJECTS AND GENERAL DESCRIPTION OF THE INVENTION

Accordingly, a primary object of the present invention is to provide a compact, inexpensive, and easy-to-operate sensing device for accurately and reproducibly detecting and quantitatively determining the level of gaseous pollutants in a specific entironment.

Another object of this invention is to provide compact, inexpensive, and easy-to-operate sensing devices for accurately and reproducibly detecting and quantitatively determining low concentrations of noxious gases in the presence of high concentrations of CO.

Another object of this invention is to provide a method for electrochemically detecting low concentrations of noxious gases in a gaseous medium.

The aforementioned objects of the present invention are obtained by an electrochemical sensing device comprising an electrochemical cell comprising a sensing electrode, a counterelectrode, an aqueous electrolyte in contact with said sensing electrode and counterelectrode, said sensing electrode comprising a carbon-supported gold catalyst, means for exposing said sensing electrode to the gas to be detected, means electrically coupled to said sensing electrode for maintaining said sensing electrode at a potential of about 0.4 volt to about 1.5 volt with respect to the potential of the reversible hydrogen couple in the electrolyte of said cell and means for measuring current flowing between said sensing electrode and said counterelectrode which measured current is a measure of the concentration of the noxious gas being detected.

An important feature of the invention is the surprising discovery that use of carbon supported gold electrodes as the sensing electrode in the electrochemical cell provides unexpectedly greater selectivity for noxious gases such as NO, $NO_2$, $H_2S$, $SO_2$, $CH_3SH$, $C_2H_5SH$ and the like in the presence of CO than do prior art sensing electrodes, including non-supported gold electrodes. By way of illustration, when the carbon supported electrode is used as the sensing or working electrode in the apparatus of the invention typical discrimination ratios for $NO_2$ and $H_2S$ in the presence of Co are $-10,000/1$ and $20,000/1$, respectively. Considering the typical ambient concentrations of 10 ppm CO, 20 ppb $NO_2$ and 5 ppb $H_2S$, 10 ppm CO will give in the apparatus of the invention a reading equivalent to $-1$ ppb $NO_2$ (a 5% error in $NO_2$ signal and equivalent to 0.5 ppb $H_2S$ (a 10% error in $H_2S$ signal). A comparison between these percent errors with those obtained and noted above when a non-supported gold sensing electrode is used demonstrates that in the presence of CO use of the carbon supported gold electrode provides 10 times the selectivity of the unsupported gold electrode for both $NO_2$ and $H_2S$.

The unexpected nature of the invention is understood by the fact that in the electrochemical detection of the noxious gases with which the invention is concerned the catalytic activity of carbon supported gold is equivalent to but no better than non-supported gold. However, it has been discovered that insofar as the electrooxidation of CO is concerned this essential equivalence in catalytic activity between carbon supported and unsupported gold electrodes does not hold true. Rather it has been surprisingly found that the catalytic activity of the carbon supported gold electrodes is significantly less than that of unsupported gold electrodes. As a consequence, the sensor of the invention retains the desired high catalytic activity for the electrochemical reaction of the noxious gases desired to be detected that characterizes unsupported gold electrodes but without the adverse effects on selectivity associated with the latter because of their ability to effect significant electrooxidation of the CO normally present.

The sensing electrode of the invention may take any suitable form. For instance, the carbon support may be solid, porous, absorbent carbon of any desired shape, form and size onto which the gold catalyst is deposited. Such electrodes may be prepared for example by impregnating the absorbent carbon with a solution of a gold salt decomposable to gold oxide, heating the impregnated carbon at an elevated temperature sufficient to effect said decomposition to the oxide followed by heating gold in the presence of hydrogen to reduce the gold oxide to the catalytically active free metal.

The preferred sensing electrodes comprise carbon particles containing catalytic amounts of gold provided thereon by any suitable technique known in the art of catalyst preparation. A preferred method involves forming a solution of metallic gold or a salt thereof, impregnating carbon particles with the resulting solution, drying the impregnated carbon particles followed by heating at elevated temperatures, usually of at least 500° F., preferably 600° F.–800° F. in the presence of a reducing gas such as hydrogen so as to ensure conversion of the gold salt to its free metal state and provide an active catalyst. The carbon employed as the support can be any of the carbons conventionally employed as supports in the catalyst art. For instance, it can be a graphitized carbon such as Acheson No. 38 (a product of Fisher Scientific Co.) or non-graphitized carbon such as Vulcan XC-72 (a product of Cabot Corporation). The amount of gold in the carbon supported catalyst which makes up the sensing electrode of the invention may vary over a wide range but in all cases will be present in catalytic amounts, that is, in amounts that will catalyst the electrochemical reaction of the noxious gas detected, be the reaction an electrooxidation or a electroreduction. Generally, the gold will be present in an amount of about 3 to 50%, preferably 5 to 25% by weight of the supported catalyst. A particularly preferred form of the sensing electrodes comprise carbon supported gold catalyst particles bonded to a suitable hydrophobic material such as unsintered polytetrafluoroethylene (PTFE) to provide a lightweight diffusion electrode. The hydrophobic material may take the form of a binder for the catalyst, a sheet support therefor or both. For instance, particles of carbon supported gold catalyst may be deposited as a layer directly to the surface of a hydrophobic sheet support or the supported gold particles may be admixed with a suitable hydrophobic binder and applied to a porous metal, porous hydrophobic sheet and the like. Suitable hydrophobic binders and/or support substrate materials include hydrophobic fluorocarbons such as polytetrafluoroethylene, polychlorotrifluoroethylene, polymeric silicones or the like, as well as less hydrophobic materials including polyacrylonitrile, polyvinylchloride, polyvinylalcohol, carboxymethyl cellulose, or the like. As will be apparent to one skilled in the art, when the carbon supported catalyst is applied to a hydrophobic substrate such as PTFE, the hydrophobic material must be oriented in the cell so that the catalyst is in contact with the electrolyte and the surface of the hydrophobic substrate contacts the gas sample.

The sensor of the invention can be either a two electrode system or a three electrode system. Of the two systems, the three electrode system is preferred and includes a reference electrode in addition to the sensing electrode and counterelectrode. The reference electrode of the electrochemical cell must be capable of maintaining a relatively constant potential in the environment of the electrochemical cell. Preferred reference electrodes are Pt-catalyzed air electrodes. The third or reference electrode can be positioned between the sensing electrode and counterelectrode, or it can be positioned on the same plane or substrate as the sensing electrode or counterelectrode. Preferably, however, in order to obtain greater compactness of the cell and due to optimum ion-transfer characteristics, and the like, the counterelectrode and the third or reference electrode will be part of a common substrate. It is only necessary that the electrodes of the electrochemical cell be in contact only via the electrolyte. Thus, a polymer substrate such as polytetrafluoroethylene can have two separate and distinct portions coated with a catalytic material such as platinum, or an admixture of platinum and PTFE particles. The entire substrate will, therefore, function as both the counterelectrode and reference electrode. As will be more fully apparent hereinafter, various designs or lay-outs can be used.

Reference electrode, as the term is used herein, defines an electrode at which no, or substantially no, current flows. Accordingly, the reference electrode and sensing electrode must be connected through electronic circuitry, or the like, to preclude or minimize current flow between the reference electrode and sensing electrode, so as to define and maintain a known reference potential. Although it is virtually impossible to completely eliminate current flow, the reference potential cannot show extensive drift, i.e., more than about ± 25 mV; or rapid drift, i.e., more than ± 5 mV, over a period of ten seconds. If extensive or rapid drift occurs, a false reading as to the quantity of the detected gas may be obtained. As is apparent, the actual extent of current drift depends upon the accuracy of the measurement needed. If high accuracy is unnecessary, a greater current drift can be tolerated.

The specific structure of the counterelectrode employed in the electrochemical cell is not critical. Where the sensing electrode of the sensor catalyzes electrooxidation of the gas to be detected it is only essential that the counterelectrode be comprised of a material at which electrochemical reduction occurs. On the other hand, where the sensing electrode catalyzes electroreduction of the gas to be detected, it is only essential that the counterelectrode be comprised of a material at which electrooxidation occurs. In most instances, the selection of the particular counterelectrode will depend upon whether a 2-electrode or 3-electrode system is employed. When a 3-electrode system is utilized the cathodic and anodic counterelectrodes are generally noble metal electrodes such as platinum or gold electrodes. When a 2-electrode system is utilized the preferred cathodic counterelectrode is lead dioxide or manganese dioxide and the preferred anodic counterelectrode is a hydrogen electrode.

One of the problems which may be encountered in the utilization of measuring equipment such as the cell of the present invention relates to the fact that an oxygen-water redox couple will be potentially available within the electrochemical cell to generate undesired current in the external circuit which current is not derived from reaction of the noxious gas to be detected. Such a redox couple results from oxygen contained in the incoming atmospheric air and water contained in the electrolyte. For example, under certain circumstances water may become oxidized at the sensing electrodes of the cell thereby generating current in the external circuit that would not be distinguishable from the current generated by the noxious gas reaction. Likewise, oxygen may undergo reaction at the sensing electrode thereby similarly generating undesired current. For this reason, means are provided the electrochemical cell of the invention for maintaining the sensing electrode at a potential of about 0.4 V to 1.5 V with respect to the potential of the reversible hydrogen couple in the electrolyte of the cell. It has been found that a fixed potential within this range creates a condition whereby the oxygen-water couple produces in the external circuit no discernible current relative to the current produced by the reaction of the noxious gas to be detected.

The potential selected within this range wil depend on the particular gas to be detected. For instance, in the detection of nitric oxide (NO) the potential should be maintained at from about 0.9 to 1.5. In the case of the detection of $NO_2$ by electroreduction the potential should be maintained from about 0.4 V to 1.0 V. The sulfur-containing gases such as $H_2S$, $SO_2$ and the mercaptans, on the other hand, can be accurately measured throughout the entire potential range.

The means for maintaining the potential within the prescribed range can be any suitable means. In the case of a 3-electrode system it can be a potentiostat and in the case of a 2-electrode system it can be a potential-divider.

The electrolyte employed in the electrochemical cell of the present invention can be either an aqueous acid or an aqueous alkaline solution. The electrolytes can be free flowing or trapped in a suitable matrix. In the event a matrix is employed, the matrix material must be sufficiently hydrophilic to permit continuous wetting of the sensing electrode and the counterelectrode surfaces as well as the surface of the third or reference electrode when a three electrode system is employed. Materials such as asbestos, Kraft paper, polyvinylalcohol, polyvinylchloride which has been treated to render it hydrophilic or the like can be selected.

The means for measuring the current flowing from the sensing electrode to the counterelectrode can be any suitable readout means such as an ammeter. The reading taken at the ammeter will be representative of the electrodhemical reaction occurring at the sensing electrode and of the quantity of material reacted. The ammeter may be readily calibrated in a known manner to provide determination of the quantity of noxious gas occurring in the air sample taken.

In operation, the detecting unit of the invention will include sample intake means and means to draw the flow of the gas sample through the cell, preferably at a controlled flow rate. The control of the flow rate of the sample can be accomplished in various ways. In most instances, however, the means for drawing the gas through the intake means into the cell will effectively pass a predetermined quantity of gas per unit time to a predetermined surface area of the sensing electrode, thus assuring continuous accuracy in the quantitative measurement. Preferably, the quantity of gas fed to the sensing surface is controlled by a constant flow control means of the conventional type which feeds the gas sample to the electrochemical cell at a constant rate. Pumping or suction means are normally employed to draw the gas sample through the intake means, the electrochemical cell, and flow control means in metered amounts. Preferably, the sensing chanber will define a labyrinthine path as is described in the electrochemical cell of U.S. Pat. No. 3,776,832 hereby incorporated by reference, through which the gas sample is passed to the working electrode surface. Other designs can be employed, it only being essential that the geometric working or sensing electrode surface area remains constant, or substantially constant, and is fed with a predetermined quantity of gas over a predetermined period of time. In this regard, it is to be noted that insofar as the actual gas being detected is concerned, it is immaterial whether the flow rate is high or low.

The sensing device of the present invention can be utilized to detect and measure the presence of the noxious gases generally, i.e. without differentation, or it can be used to detect and measure the presence of but one of the noxious gases specifically.

When it is desired to detect but one of the noxious gases alone, that is, to the exclusion of other gases present in the gas medium containing the gas to be detected, it may be necessary in addition to selecting a suitable fixed potential to employ suitable filter or scrubber means between the sample intake and the electrochemical cell in order to remove the interfering gases. For instance, when it is desired to detect and measure NO to the exclusion of $NO_2$ and $H_2S$, the $NO_2$ and $H_2S$ can be removed from the gas sample by placing a suitable filter or scrubber means between the sample intake and electrochemical cell. Suitable filters or scrubbers for $NO_2$ are adsorbents such as fire brick impregnated with triethanolamine, Mallcosorb and the like, and suitable $H_2S$ filters are lead acetate and mercuric chloride.

In many instances the noxious gas to be detected will be present in the gas medium in such high concentrations compared to the other noxious gases that it will be unnecessary to remove the latter or otherwise modify the instrument, since the signal given by the latter gases will be insignificant compared to that given by the noxious gas to be detected.

The housing of the electrochemical cell can be made of any suitable material which does not form soluble oxidizable products. Plastics such as the olefinic polymers are preferred. The housing is to be designed to permit the sensing electrode to have an area exposed to ambient air.

BRIEF DESCRIPTION OF THE DRAWINGS

The detecting device of the present invention will be more readily apparent from the accompanying drawing wherein like numerals are employed to designate like parts. While the arrangement to be described is designed especially for the detection and monitoring of NO gas in a 3-electrode system, it should be understood that essentially the same device with appropriate modification of filters and potentials can be used for the detection and monitoring of other noxious gases in the presence of CO. In addition it should be understood that a 2-electrode system modified as described above by one of ordinary skill in the art can likewise be similarly employed.

In the drawing.

DETAILED DESCRIPTION OF PREFERRED EMBODIMENT

Figure 1:
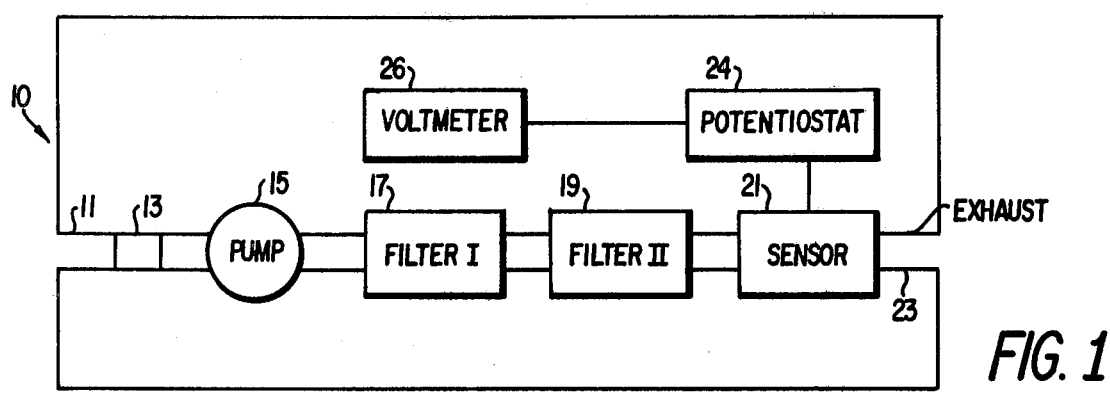
FIG. 1 is a diagrammatic view in block form of a preferred three-electrode sensing device suitable for use in the detection and measuring of NO gas in the atmosphere.

More specifically, referring to FIG. 1, the detecting device for the measurement of NO is positioned within a housing 10. The device includes a sample intake means 11 in direct communication with a flow meter 13 which in turn is in communication with a pump 15. The pump 15 communicates with a filter 17 containing, for instance, mercuric chloride for the adsorption of $H_2S$. Filter 17 is in direct communication with filter 19 containing, for instance, fire brick impregnated with triethanolamine for the removal of $NO_2$. Filter 19 in turn is in direct communication with sensor 21. Gas flowing through the sensor 21 exits device via exhaust 23. The sensor is provided with a potentiostat 24 for maintenance of the fixed relative potential between the anode and the reference electrode of sensor 21 and a voltmeter 26. The potentiostat is hooked up to an electronic circuit described below which includes an amplifier and voltmeter.

Figure 2:
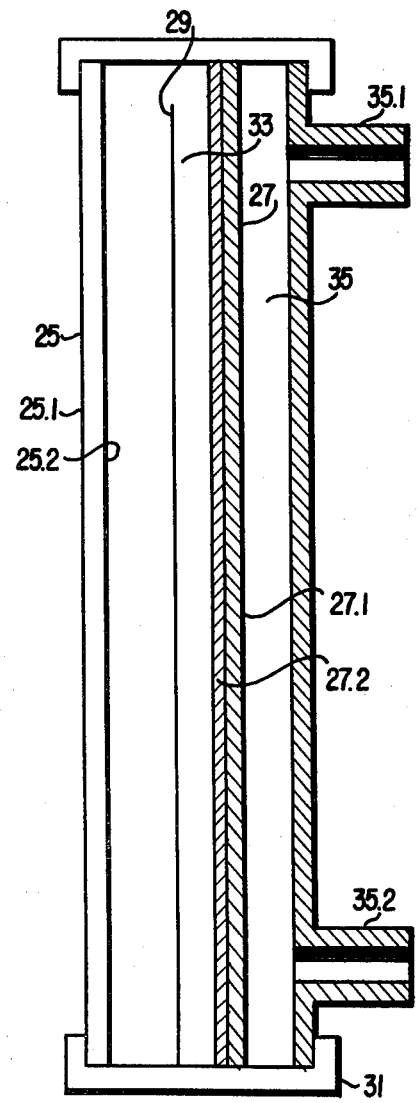
FIG. 2 is a cross-sectional view of the electrochemical cell of the detector unit.

Electrochemical cell 21 as seen most clearly from FIG. 2, will include a cathode 25, an anode 27 (sensing electrode) and a third or reference electrode 29, all positioned within a housing 31. In the embodiment of FIG. 2, the cathode, anode, and third electrode are in contact with a free-flowing electrolyte 33. Adjacent anode 27 is reactant chamber 35 having reactant gas inlet 35.1 which is in direct communication with intake 11 and outlet 35.2. In the embodiment shown, cathode 25 is in direct communication with atmospheric air. Both the anode and cathode are lightweight electrodes comprising a hydrophobic plastic substrate 27.1 and 25.1 in direct contact with reactant chamber 35 in the case of the anode, and with the ambient environment in the case of the cathode and catalytic layers 27.2 and 25.2 respectively, which catalyst layers are in contact with the electrolyte of the cell. The catalytic layer 27.2 of the sensing electrode 27 is a layer of carbon particles containing 15% by weight gold. The gold supported on carbon catalyst is prepared in the following manner:

A stock solution is prepared by dissolving gold metal in 250 mls of aqua regia and diluting to 1 liter such that the solution contains 1.09 g of gold/ml of solution. The carbon is then stirred in a solution containing 1.38 ml of the gold stock solution and 250 mls of water. This solution is evaporated to dryness while stirring over a period of 5 to 6 hours. Drying is completed by heating the gold salt-carbon mixture at 110° C. in an oven overnight. Finally the mixture is placed in a combustion boat, and the gold is reduced by heating to 700° F. for 2 hours in an atmosphere of hydrogen.

The gold on carbon catalyst particles thus prepared are then mixed with a dispersion of polytetrafluoroethylene particles to provide a mixture which is applied to the hydrophobic substrate 27.1 as a layer at a loading of preferably 5-50 mg/cm², more preferably 5-30 mg/cm². The ratio of carbon supported gold to PTFE is preferably 10 to 3 on a weight basis. Catalytic layer 25.2 of the cathode 25 comprises a mixture of platinum and polytetrafluoroethylene. Reference electrode 29 is a porous, platinum catalyzed PTFE diffusion electrode which is approximately 7 mils thick. A fixed potential of 1.5 volts with respect to a reversible hydrogen electrode in the same electrolyte is maintained on the anode by means of the reference electrode through the potentiostat 24. The anode, cathode and reference electrode of the cell are connected through the electrical circuit, shown in FIG. 3. The electrochemical cell of the sensor is connected to the circuitry so that the polarity of the working electrode (anode) to the counter electrode (cathode) is positive.

Figure 3:
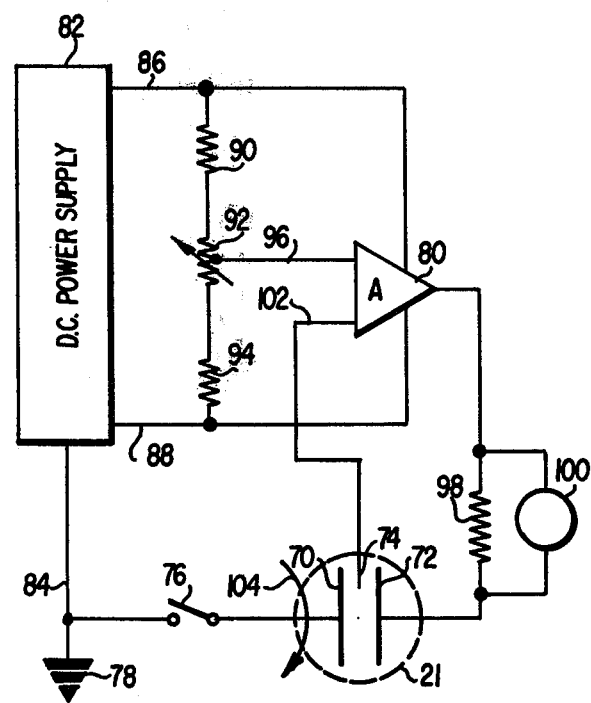
FIG. 3 is a schematic diagram of a potentiostat circuit for controlling operation of the cell and particularly as applied in maintaining a fixed potential between the working electrode and a reference electrode in a three-electrode system.

The circuitry whereby the maintenance of a fixed relative potential between the working electrode and reference electrode is shown in FIG. 3. FIG. 3 depicts a potentiostat circuit which is generally arranged in accordance with conventional principles within the knowledge of those skilled in the art and which enables the maintenance of the fixed relative potential between the working electrode and the reference electrode without development of current flow therebetween. The circuit also operates to enable appropriate current flow in the external circuit between the working electrode and the counter electrode when the gas to be detected is reacted within the electrochemical cell.

In FIG. 3, the electrochemical cell 21 is shown schematically as comprising an anode 70, a cathode 72, and a reference electrode 74, with the anode connected through a switch 76 to ground potential 78. The circuit basically comprises an operational amplifier 80 having both the reference electrode 74 and the cathode 72 connected thereto. A DC power supply 82 having a connection 84 to ground potential 78 is connected to the amplifier 80 through leads 86 and 88 with resistors 90, 92 and 94 connected thereacross in parallel between the power supply 82 and the amplifier 80. Resistor 92 comprises a rheostat and is connected to the amplifier 80 through a lead 96 whereby adjustment of the resistor 92 enables adjustment of the fixed relative potential which is to be maintained between the reference electrode 74 and the anode 70. The cathode 72 is connected to the amplifier 80 through a resistor 98 having a voltmeter 100 connected thereacross. The reference electrode 74 is connected to the operational amplifier 80 through a lead 102 and as the relative potential between the reference electrode 74 and the anode 70 develops a tendency to vary from the fixed level established by adjustment of the rheostat 92, the amplifier 80 operates through a negative feedback to maintain constant the relative potential between the anode 70 and the reference electrode 74. The factor creating the tendency to alter the anode-reference electrode fixed relative potential is developed as a result of reaction at the anode 70 of the impurity to be detected, i.e. oxidation of NO contained within the gas sample flowing across the face of the anode 70 as indicated by the arrow 104. The output current of the operational amplifier 80 will pass through the resistor 98 and will be a result of and related to the level of oxidation occurring at the anode 70. Therefore, the reading taken at the voltmeter 100 will be representative of the oxidation reaction occurring at the anode 70 and the quantity of material oxidized.

In operation, therefore, assuming the desirability of measuring the concentration of NO in the atmosphere, the atmospheric air containing the noxious gas is introduced at a metered rate into the sensor. The sample is passed through filters 17 and 19 for removal of $H_2S$ and $NO_2$. In the NO sensor the air sample passes over the anode therein setting off electrooxidation of the NO impurity contained therein. This electrochemical reaction produces a current in the external circuit of the cell thereby enabling detection and measurement of the impurity concentration as by use of a voltmeter.

It is claimed:

1. An apparatus for detecting and measuring noxious gases selected from the group consisting of nitric oxide, nitrogen dioxide, sulfur dioxide, mercaptans and hydrogen sulfide, in the presence of carbon monoxide comprising in combination intake means, an electrochemical cell, means for drawing said gas through said intake means and into said electrochemical cell, the electrochemical cell comprising a sensing electrode, a counterelectrode and an aqueous electrolyte in contact with said sensing electrode and counterelectrode, said sensing electrode comprising a carbon supported gold catalyst, means for exposing said sensing electrode to said gas, means electrically coupled to said sensing electrode for maintaining said sensing electrode at a fixed potential of about 0.4 volt to about 1.5 volt with respect to a reversible hydrogen electrode in said electrolyte of said electrochemical cell and means for measuring current flowing from said sensing electrode to said counterelectrode which measured current is a measure of the concentration of the noxious gas being detected.

2. The apparatus of claim 1 wherein the catalyst is in the form of carbon particles containing catalytic amounts of gold.

3. The apparatus of claim 2 wherein the carbon-equipped gold catalyst particles are bonded to a hydrophobic material to provide a diffusion electrode.

4. The apparatus of claim 3 wherein the catalyst particles contain 3 to 50% by weight gold.

5. The apparatus of claim 3 wherein the catalyst particles contain 5 to 25% by weight gold.

6. The device of claim 3 wherein the hydrophobic material is polytetrafluoroethylene.

7. The device of claim 6 including means between the intake and said electrochemical cell for the removal of $H_2S$ gas.

8. The device of claim 7 including means between the intake and said electrochemical cell for the removal of $NO_2$ gas.

9. The apparatus of claim 3, wherein the carbon supported gold catalyst particles are admixed with polytetrofluoroethylene and applied to a porous hydrophobic sheet to form a light weight diffusion electrode.

10. A sensing device for detecting and measuring noxious gases in the presence of carbon monoxide which comprises an electrochemical cell comprising a sensing electrode, a counterelectrode, and an aqueous electrolyte in contact with said sensing electrode and counterelectrode, said sensing electrode comprising a carbon-supported gold catalyst, means for exposing said sensing electrode to said gas, means electrically coupled to said sensing electrode for maintaining said sensing electrode at a fixed potential of about 0.4 volt to about 1.5 volt with respect to a reversible hydrogen electrode in said electrolyte of said electrochemical cell and means for measuring current flowing from said sensing electrode to said counterelectrode which measured current is a measure of the concentration of the noxious gas being detected.

11. The device of claim 10 wherein the carbon-supported gold catalyst is in the form of particles bonded to a hydrophobic material to provide a diffusion electrode.

12. The device of claim 10 wherein the hydrophobic material is polytetrafluoroethylene.

13. The device of claim 11, wherein the carbon-supported gold catalyst particles are admixed with polytethafluoroethylene and applied to a porous hydrophobic sheet to form a light weight diffusion electrode.

* * * * *